United States Patent [19]

Schoendorfer et al.

[11] Patent Number: 4,740,313
[45] Date of Patent: Apr. 26, 1988

[54] METHOD OF FILTERING USING A ROTATING AND OSCILLATING SPINNER

[75] Inventors: Donald W. Schoendorfer, Santa Ana; William F. McLaughlin, Newport Beach, both of Calif.

[73] Assignee: Baxter Travenol Laboratories, Inc., Deerfield, Ill.

[21] Appl. No.: 921,367

[22] Filed: Oct. 20, 1986

Related U.S. Application Data

[62] Division of Ser. No. 764,632, Aug. 12, 1985, Pat. No. 4,670,147.

[51] Int. Cl.[4] ............................................. B01D 13/00
[52] U.S. Cl. .................................... 210/651; 210/781; 210/90
[58] Field of Search ....................... 210/90, 433.2, 651, 210/321.1, 649, 781

[56] References Cited

U.S. PATENT DOCUMENTS

| 3,356,346 | 12/1967 | Landsberger . |
| 3,634,228 | 1/1972 | Latham, Jr. . |
| 4,083,788 | 4/1978 | Ferrara . |
| 4,522,713 | 6/1985 | Nussbaumer et al. . |
| 4,534,863 | 8/1985 | Bacon et al. . |

OTHER PUBLICATIONS

R. J. Forstrom et al.; "Formed Element Reposition onto Filtering Walls," Trans. Am. Soc. Artif. Int. Orgs., vol. XXI (1975), pp. 602–607.
Dorson et al.; WO82/03567; 10/1982.
Lopez-Leiva, "Ultra Filtration at Low Degrees of Ion Conc. Tech. Possibilites", 1980.

*Primary Examiner*—Frank Sever
*Attorney, Agent, or Firm*—Paul C. Flattery; Gregory L. Roth; Bradford R. L. Price

[57] ABSTRACT

A disposable diagnostic plasma filter dispenser includes a low cost disposable container and a rotor drive for rotationally energizing a rotor within the container. The disposable container is particularly suitable for drawing and dispensing blood samples for clinical analysis and includes a tube shaped outer wall having a frangible dispenser outlet cover, a close fitting inner tube supporting a filter membrane and a unitary rotor disposed for axel free rotation and axial translation within the inner tube in response to energization from the rotor driver. The rotor produces vortex enhanced filtration while maintaining a flow of filter fluid through the filtration gap and creating a transmembrane pressure.

8 Claims, 8 Drawing Sheets

(TIME SECONDS)

METHOD OF FILTERING USING A ROTATING AND OSCILLATING SPINNER

This is a divisional of co-pending application Ser. No. 764,632 filed on Aug. 12, 1985, now U.S. Pat. No. 4,670,147.

BACKGROUND OF THE INVENTION

This invention provides a low cost disposable filter dispenser which quickly and conveniently separates and dispenses a small quantity of fluid such as blood plasma or blood serum which may be used for laboratory analysis or other purposes. This new filter dispenser minimizes the possibility of attendant contamination while in no way adding to the inconvenience of a donor.

Despite numerous attempts to automate the process of drawing blood samples and separating plasma or serum therefrom for analysis, the process remains essentially manual. In contrast, much greater success has been attained in automating the analysis of the samples once they have been drawn and separated.

At the present time, the most commonly used procedure for drawing blood samples starts with use of a cylindrical holder 10 and an evacuated container 11 called a "Vacutainer," as illustrated in FIG. 1. The generally cylindrical holder has a closed end 12A and an opposite open end 13B for receiving the container 11. A plastic support 13 is molded around a double ended phlebotomy needle 14 near its center and threadingly engages the closed end 12A of the holder 10. The plastic support 13 has a bulbous protrusion 15 on its interior end, which receives in tight fitting relationship an upper end of a rubber sock 16. Normally, the closed end of the sock 16 encompasses and protects the end of the needle 14 retained in the holder 10.

In operation, the holder 10 is used when inserting the outer end of the needle 14 into a vein of a donor. At this time, sock 16 serves to prevent leakage of blood into the interior of holder 10. Next, the evacuated container 11, having a rubber stopper 17, is inserted, stopper end first, into the open end of holder 10. The intension end of the needle 14 forced through the rubber stopper piercing both the rubber sock 26 and stopper 17. The vacuum within container 11 then causes blood to be withdrawn through needle 14 and into the container 11. Typically, several of these "Vacutainers" may be successively inserted into the holder 10 and filled with blood before the outer end of needle 14 is withdrawn from the donor.

When different containers have been filled, they are then typically used for different analytical tasks. For example, one container might contain an anticoagulant such as tri-sodium citrate, ACD or heparin and have plasma separated therefrom. In another container the blood might be allowed to clot so that serum can be separated for analysis.

Once the samples are drawn, they are typically labeled and sent to a laboratory. At the laboratory, the containers are centrifuged for 5-10 minutes at 900-2000 g's. A laboratory technician must then carefully remove the rubber stopper 17 from its container 11 without disturbing the contents. A disposable non-reusable pipette is used to draw off plasma or serum and the rubber stopper 17 is placed back in the container 11 prior to disposal of the container 11 and its contents.

This widely used procedure is thus quite slow, and inconvenient. Both the person drawing blood and the laboratory technician are exposed to possible contamination. The needle, the "Vacutainer", the pipette and a tray or dish receiving the analysis fluid from the pipette must all be disposed of, adding to costs.

U.S. Pat. No. 4,343,705 for "Biological Liquid Fractionation Using Opposite Flow Directions Across A Membrane" by Legg teaches one attempt at improving upon the blood withdrawal and separation process. Legg pours the blood into an open receptacle from which it is aspirated back and forth across one side of a flat sheet membrane filter. The other side of the filter communicates with the receptacle for the plasma filtrate. The system requires expensive pumps, valves and automatic controls. The disposables include the receptacles and the filter membrane, and are thus relatively expensive. The laboratory technician has essentially the same risk of contamination as where the centrifuge and pipette are used.

Many attempts have been made to incorporate the fractionation process directly into the "Vacutainer" or similar receptacle. Examples of U.S. patents describing such attempts are listed as follows:

U.S. Pat. No. 3,508,653, Coleman
U.S. Pat. No. 3,539,300, Stone
U.S. Pat. No. 3,682,596, Stone
U.S. Pat. No. 3,761,408, Jae Yoon Lee
U.S. Pat. No. 3,814,079, LeRoy, Sr.
U.S. Pat. No. 3,850,174, Ayres
U.S. Pat. No. 3,920,557, Ayres
U.S. Pat. No. 3,926,521, Ginzel
U.S. Pat. No. 3,960,727, Hochstrasser
U.S. Pat. No. 3,965,889, Sachs
U.S. Pat. No. 3,972,812, Gresl, Jr.
U.S. Pat. No. 4,012,325, Columbus
U.S. Pat. No. 4,035,294, Landers et al
U.S. Pat. No. 4,052,320, Jakobowicz
U.S. Pat. No. 4,083,788, Ferrara
U.S. Pat. No. 4,131,549, Ferrara
U.S. Pat. No. 4,303,530, Shah et al.
U.S. Pat. No. 4,443,345, Wells In each case, high cost, inconvenience of use or some other disadvantage has prevented the disclosed technique from receiving widespread acceptance. It is desirable to employ the widely accepted vacuum enclosure approach for withdrawing blood, but it is far preferable to be able to fractionate the needed small amounts of filtrate directly on site, virtually immediately and without additional handling.

It is known to use a rotary system in conjunction with a membrane filter to fractionate a liquid suspension so as to obtain a desired filtrate with high throughput, reliability and freedom from contamination. One example of such a system is shown in application Ser. No. 591,925 filed Mar. 21, 1984 by Donald W. Schoendorfer for "Method and Apparatus for Separation of Matter". In this system the rotary spinner, which may include a surface filter membrane or be encompassed at least in part by a filter membrane, is arranged and operated to establish enhanced vortices of the Taylor type, which provide a constant sweeping motion over the filter membrane together with high shear to establish a high throughput, non-clogging filtration action. This system is particularly effective in hemapheresis applications because it employs a low cost, non-contaminating disposable that does not hemolyze or otherwise damage the fragile blood constituents. However, this disposable still has much greater capacity and a larger and therefore more costly membrane area than are needed for most clinical applications. Even if scaled down it would require a separate procedure to transfer blood and larger and more extensive drive, control and pumping units than are desired.

SUMMARY OF THE INVENTION

A fast, low cost and extremely convenient fluid separation system in accordance with the invention includes a disposable fluid container such as an evacuated container for drawing blood and a rotor driver having a magnetic head for magnetically coupling to a rotor within the container. The container includes a tubular outer wall and a closure element such as a fracture tip that can be selectively opened to dispense filtrate fluid through the outer wall.

Interior to the outer wall is disposed a cylindrical inner tube which supports a membrane filter. The interior of the inner tube is sealed from the exterior thereof except for filter holes which are covered by the filter membrane. Filtrate fluid is thus permitted to pass through the filter and the filter holes to the exterior side of the inner tube where the inner tube is shaped to assure communication channels between the filter holes and a bottom aperture that is temporarily sealed by the closure element.

A generally cylindrical, magnetically driven rotor is disposed for rotation within the interior of the inner tube. The rotor driver generates externally of the container, magnetic drive forces which engage and rotate the rotor and cyclically generate a shuttle motion to axially translate the rotor up and down inside the inner tube to force fluid to flow between a small gap between the periphery of the rotor and the filter membrane. This shuttle motion helps create a pressure across the filter membrane to facilitate filtrate flow through the membrane. The combination of relative rotation and fluid flow through the small gap induces a vortex enhanced filtration action by the membrane filter.

The rotor drive includes a magnetic head having two pair of upper and two pair of axially displaced lower pole pieces. An energization control circuit magnetically energizes the pole pieces to create a rotating magnetic field which couples to the magnetic field of the rotor to induce self-centering rotation within the container. Oscillating energization of the upper and lower sets of pole pairs causes the axial shuttling of the rotor in addition to rotation. This creates a pumping action to force fluid between the outer periphery of the rotor and the filter to attain rapid non-clogging filter action. The action is sufficiently gentle to permit filtration of plasma or serum from blood without undue hemolysis.

Special rotor designs may be alternatively utilized to induce the pumping action without the axial shuttling motion. For example, centrifugal or other pumping actions may be self generated by the rotor. This reduces the cost and complexity of the rotor driver by eliminating the requirement for third and fourth pairs of poles at an axial position spaced from the first and second pairs of poles.

BRIEF DESCRIPTION OF THE DRAWINGS

A better understanding of the invention may be had from a consideration of the following Detailed Description taken in conjunction with the accompanying drawings in which.

DETAILED DESCRIPTION OF THE INVENTION

Figure 1:
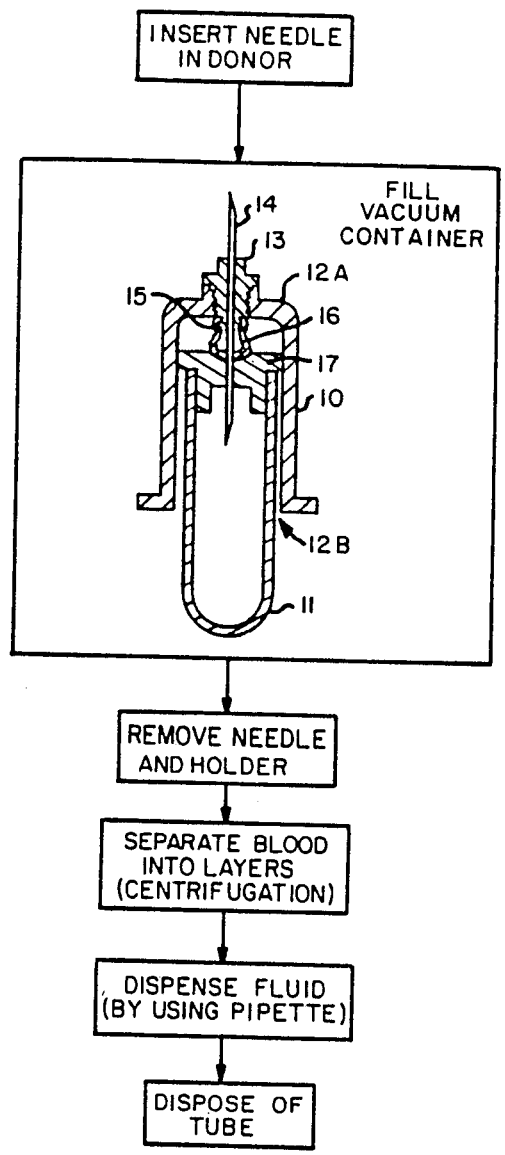
FIG. 1 is a sectional plan view of prior art apparatus and procedures for sampling, receiving and separating constituents of blood.
Figure 2:
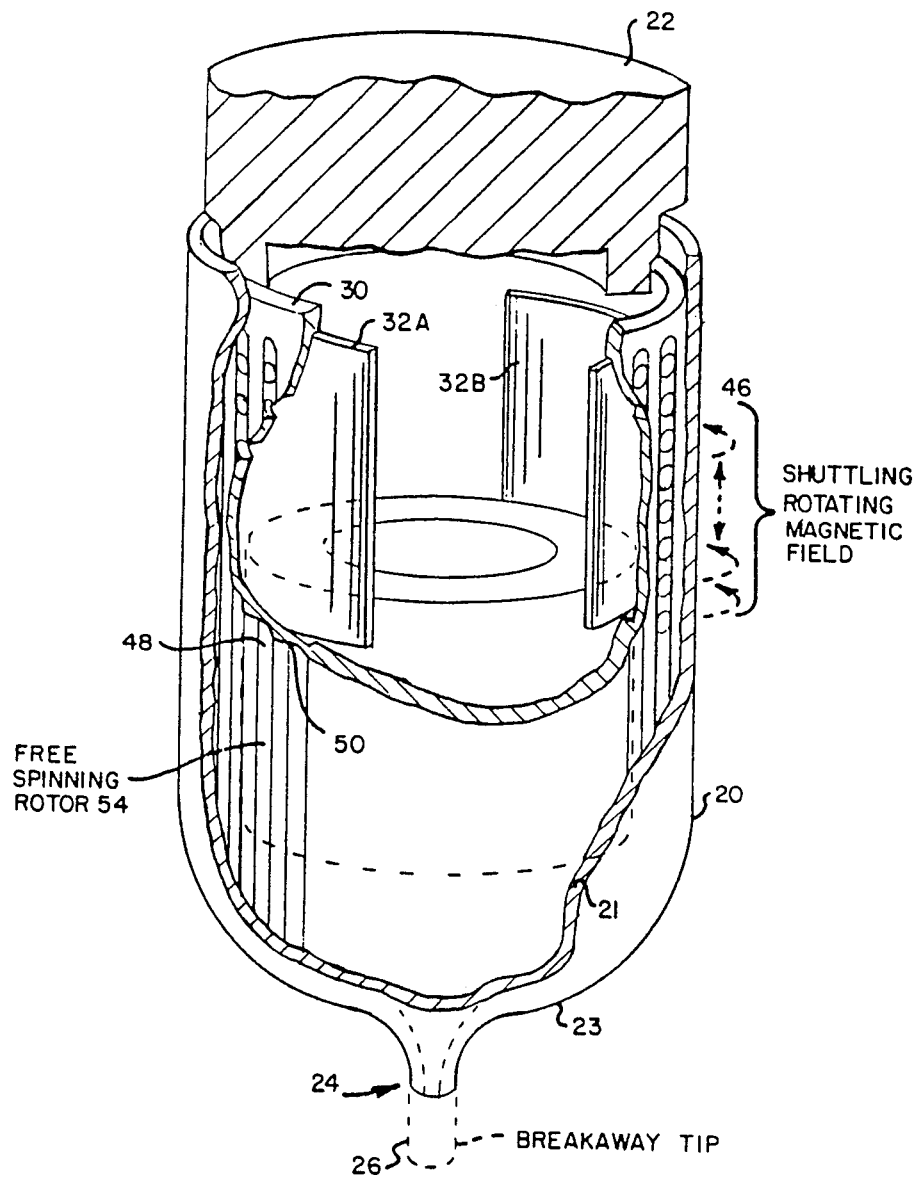
FIG. 2 is a broken away perspective view of a disposable fluid fractionation container in accordance with the invention.
Figure 3:
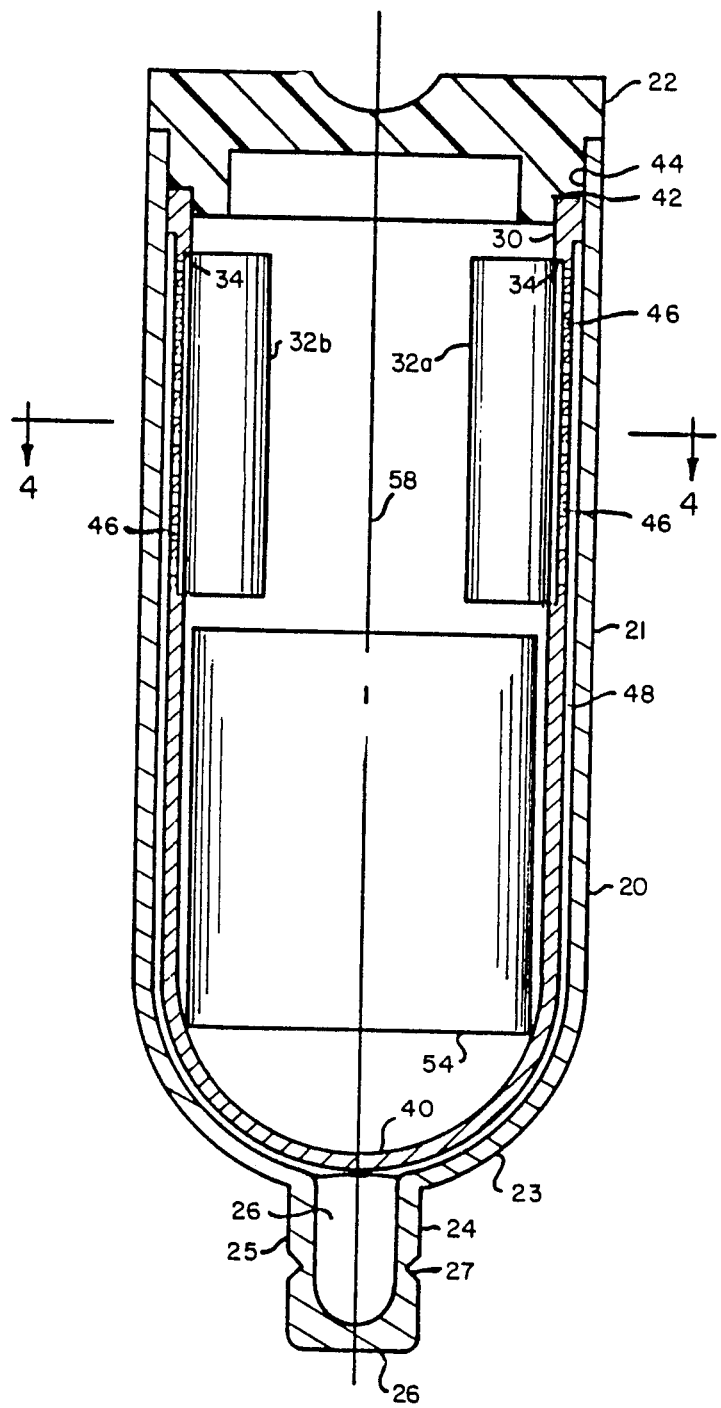
FIG. 3 is a sectional plan view of a disposable fluid fractionation container in accordance with the invention.

Referring now to FIGS. 2 and 3, a disposable fluid fractionation container 20 in accordance with the invention includes a generally cylindrical or tubular outer side wall 21 which is closed at a top end by a rubber stopper 22 and at the bottom end by a semi-spherical section 23 which joins a fracture tip 24 to the cylindrical outer wall 21 to close an outlet at the bottom of container 20. The frangible fracture tip 24 has a generally cylindrical outer wall 25 and a lower closure end 26. The upper end of the fracture tip 24 communicates with the interior of the outer container wall 21. A circumferentially extending groove 27 defines a weakness in the outer wall 25 of fracture tip 24 so that a combined twisting and pulling action upon the lower closure end 26 will cause the fracture tip to break along the circumferential groove 27 and in effect selectively open the closed bottom end of container 20 to permit fluid within container 20 to be dispensed.

Figure 4:
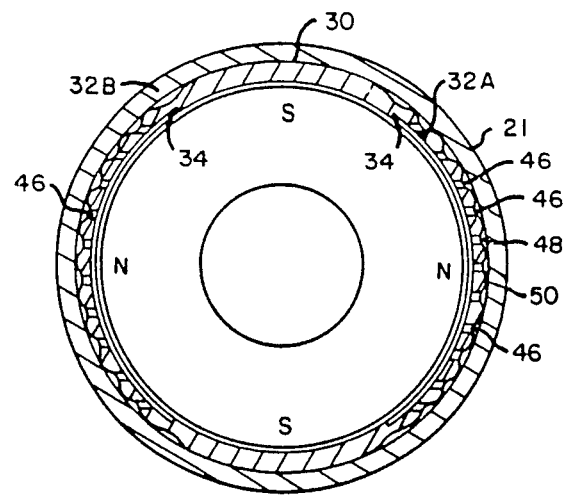
FIG. 4 is a sectional end view of the fluid fractionation container taken in the direction of the arrows 3—3 as shown in FIG. 3.

Making further reference now to FIG. 4, an inner filter support tube 30 is disposed within sidewall 21 to receive and support a thin membrane filter 32. In the present example, the membrane filter 32 is provided in two separate sections 32A, 32B, each of which extends approximately 120° about the inner circumference of the support tube 30. The two membrane sections 32A, 32B are disposed in a diametrically opposed relationship against the inner surface of the air support tube 30 within approximately the axially extending upper half thereof. In the present example, the inner tube 30 contains small recesses 34 for receiving the membrane filter sections 32, although such recesses may not be required if an ultra-thin membrane filter 32 is utilized.

The membrane filter sections 32A, 32B are circumferentially sealed to their respective recess areas 34 while a lower end 40 of inner tube 30 is closed and an upper end 42 is sealed by making engagement with the interior surface 44 of container wall 21 and by the rubber stopper 17. The only means of communication between the interior and exterior of inner support tube 30 is thus through the membrane filter sections 32A, 32B and a plurality of apertures through the cylindrical sidewall of inner tube 30. The apertures 46 are made sufficiently small to assure adequate mechanical support for membrane filter sections 32A, 32B. Since the sum of the cross-sectional areas of the apertures 46 substantially define the effective filter area of the membrane filter sections 32A, 32B, the apertures 46 are made as numerous and as close together as practical, consistent with adequate structural strength and economical manufacturing techniques for the inner support tube 30. By making the apertures 46 extend parallel to a single major diameter of the inner support tube 30, the apertures 46 can be molded into the inner support tube 30 as part of a single manufacturing process using a two-piece die. Alternatively, a more expensive die could be utilized or the apertures 46 could be bored after molding of the inner support tube 30. In this event the apertures 46 could extend radially through the inner support tube 30 and could be distributed about the entire circumference of the inner support tube 30. The membrane filter 32 would then also extend about the entire circumference of the inner support tube 30.

It is of course necessary to provide communication channels between the exterior side of the channels 46 and the dispensing aperture 26 in the bottom of the container 20. However, it is also desirable to minimize the volume of the space between the exterior of inner support tube 30 and the interior of outer wall 211. This minimization of volume is particularly desirable when the container 20 is utilized as an evacuated container for receiving blood. When the container 20 is evacuated, the entire empty inner volume including the channel spaces between the inner wall 30 and outer wall 21 is evacuated. As blood or other fluid enters the inner container, the vacuum therein lessens while the vacuum tends to remain within the volume between inner support tube 30 and the outer wall 21. This creates an undesirable trans-membrane pressure across the membrane filter 32 which tends to initiate the filter action prematurely. However, by keeping this communication channel volume sufficiently small, the brief premature filtering action remains diminimus.

The channels 48 can be advantageously defined by molding the outer periphery of inner support tube 30 with corrugations 50 which present a wavy shape in the outer surface of inner tube 30 which alternately engages the interior of outer wall 12 to support inner tube 30 and then extends radially inward to define the channel spaces 48. The apertures 46 are preferably circumferentially disposed to meet with the channel-defining small radius positions of the corrugations 50.

Disposed within the interior of inner support tube 30 is a small cylindrical pre-magnetized permanent magnet rotor 54. The rotor 54 has an axel free mounting and is thus physically contained only by the inner support tube 30. Rotor 54 is preferably magnetized with two north poles at the extremities of a first diameter and two south poles at the extremities of a second diameter that is rotated 90 degrees relative to the first diameter. Alternatively, rotor 54 may be diametrically magnetized along a single major diameter so that, in effect, one side of the rotor presents a north pole while the opposite side presents a south pole. The rotor 54 may also be non-magnetized but comprise a high permeability material and have a shaped periphery that produces a rotational torque upon engaging the externally generated rotating magnetic field. The central axis of rotor 54 shares a central axis 58 of container 10 and the rotor 54 extends axially over approximately the lower half of the container 10. The radius of rotor 54 is selected to provide a uniform radial gap of approximately 0.005 to 0.090 inch between the outer circumference of rotor 54 and the inner circumference of inner support tube 30 and the membrane filter 32. For instance, to duplicate the fluid mechanical conditions as optimized under the previously mentioned application Ser. No. 591,925 for plasmapheresis, a gap of 0.020 inch with a radius of 0.25 inch and an RPM of 6500 gives a Taylor number of 156, a Reynolds number of 550 and a shear rate of 8860/sec (assuring a specific gravity of 1.0 and a viscosity of 0.04 poise).

In operation, an externally generated rotating magnetic field causes the rotor 54 to rotate within inner support tube 30 and to also translate axially up and down within the container 20, in the vicinity of the membrane filter sections 32A, 32B. The rotational motion of rotor 54 creates a vortex enhanced flow adjacent the membrane filter sections 32A, 32B to produce improved filtering action while the repetitive up and down translations or shuttling motions produce a pumping action to continuously pump fluid through the filtration volume between the periphery of rotor 54 and the interior surface of membrane filter sections 32A, 32B. This pumping action also increases fluid pressure within inner tube 30 to provide a transmembrane pressure that is sufficient to induce filtration. The filtrate fluid passes through the filter sections 32A, 32B, the apertures 46, the channel volume 48 and eventually down to the bottom of the container 20 to the dispensing aperture 26. With the lower closure end 26 of the fracture tip 24 removed, the filtrate fluid is free to flow out of the container 20 and into a sample dish for analysis.

As is conventional with present-day sampling containers, the fractionation container 10 may initially be empty, may contain an anticoagulant such as heparin, trisodium citrate, or ACD or, alternatively, a clotting agent. If clotting is inhibited, plasma is produced as a filtrate fluid while serum is produced as the filtrate fluid if clotting is permitted to proceed.

Referring now to FIG. 4, a complete fluid separation system 60 is shown as including a container 10 mounted within a rotor driver 62. The rotor driver 62 includes an upper housing 64 mounted to a magnetic head 66.

The magnetic head 66 includes an upper support plate 68 which is secured by a plurality of axially expanding threaded bolts 70 to a magnetic core 72. A lower closure plate 74 is secured by axially extending threaded bolts 76 to the magnetic core 72. It will be seen that the upper support plate 68 has a generally cylindrical, centrally located concavity 80 on the bottom side thereof. Concavity 80 is adapted to receive a stopper 17 of a container 20 with a fit that is sufficiently tight to enable the container 20 to be supported by frictional engagement between concavity 80 and rubber stopper 17, after stopper 17 has been inserted into concavity 80. The remainder of the magnetic head 66 is generally cylindrical and has a central cylindrical bore 84 somewhat larger than the diameter of a container 20 for axially receiving a container 20 through the bottom cover plate 74 and core 72.

Figure 6:
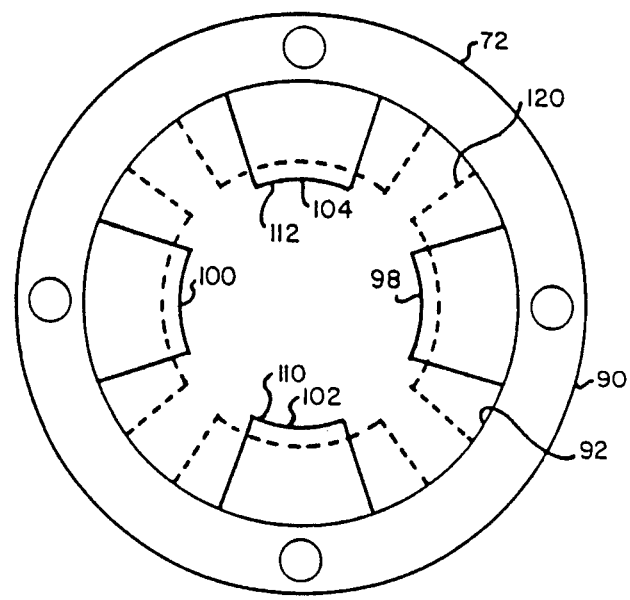
FIG. 6 is an end view of a magnetic core used in the rotor driver shown in FIG. 4.

Making further reference to a top view of core 72 which is shown in FIG. 6, the core 72 is a high permeability material core having a cylindrical outer wall 90, a cylindrical inner wall 92, and eight radially inward extending holes which are arranged in four diametrically opposed pole pairs with two pole pairs being axially positioned at an upper position 94 and two pole pairs being axially positioned at a lower position 96. A first pair of poles 98, 100 are disposed at the upper axial position 94 along with a second pair of poles 102, 104. A third pair of poles 106, 108 is axially positioned at the lower position 96 and circumferentially aligned with the first pair of poles 102, 104. Similarly, a fourth pair of poles 110, 112 is axially positioned at the lower position 96 and circumferentially aligned with the third pair of poles 102, 104 so that in FIG. 6 they remain hidden by the second pair of poles 102, 104, although numeral designations in FIG. 6 indicate their circumferential position.

A multiple turn winding 120 is provided about each pole to induce a magnetic potential therein. The windings or coils 120 are connected in series for opposing pole pairs and controlled to produce a rotating magnetic field within the container receiving cylindrical bore 84. The magnetic field is made to extend diametrically across the bore 84 and then to rotate to cause the magnetized rotor 54 of an inserted container 20 to rotate therewith. In addition, the coils at the upper position 94 and lower position 96 are selectively alternately energized to force the rotor 54 to translate up and down axially as it rotates. For example, the lower coils at the lower position 96 are initially energized to cause rotor 54 to translate upward a short distance and begin rotating. Then, the coils at upper position 98 are also energized to generate a diametric magnetic field which rotates synchronously with the magnetic field generated by the coils at lower position 96. This causes the rotor 54 to move further axially upward to a position about midway between the upper position 94 and the lower position 96. Subsequently, the coils at the lower position 96 are de-energized and the rotor 54 further moves upward to its highest position under the attractive force of the magnetic fields generated by the coils 120 at upper position 94. The cycle continues with the coils at lower position 96 being energized to move the rotor 54 somewhat downward and then with the coils at upper position 94 being de-energized to move the rotor 54 further downward to its lowest axial position. This completes one up and down shuttle cycle which is then repeated as necessary until a required amount of filtrate has been dispensed through the open bottom end of the container 10.

The upper housing 64 includes a relatively thin cylindrical sidewall 120 and an upper cap 122 which closes the upper end of sidewall 124 and is secured by a groove 126 which snaps over a circumferentially extending ridge 128 in sidewall 124.

Figure 5:
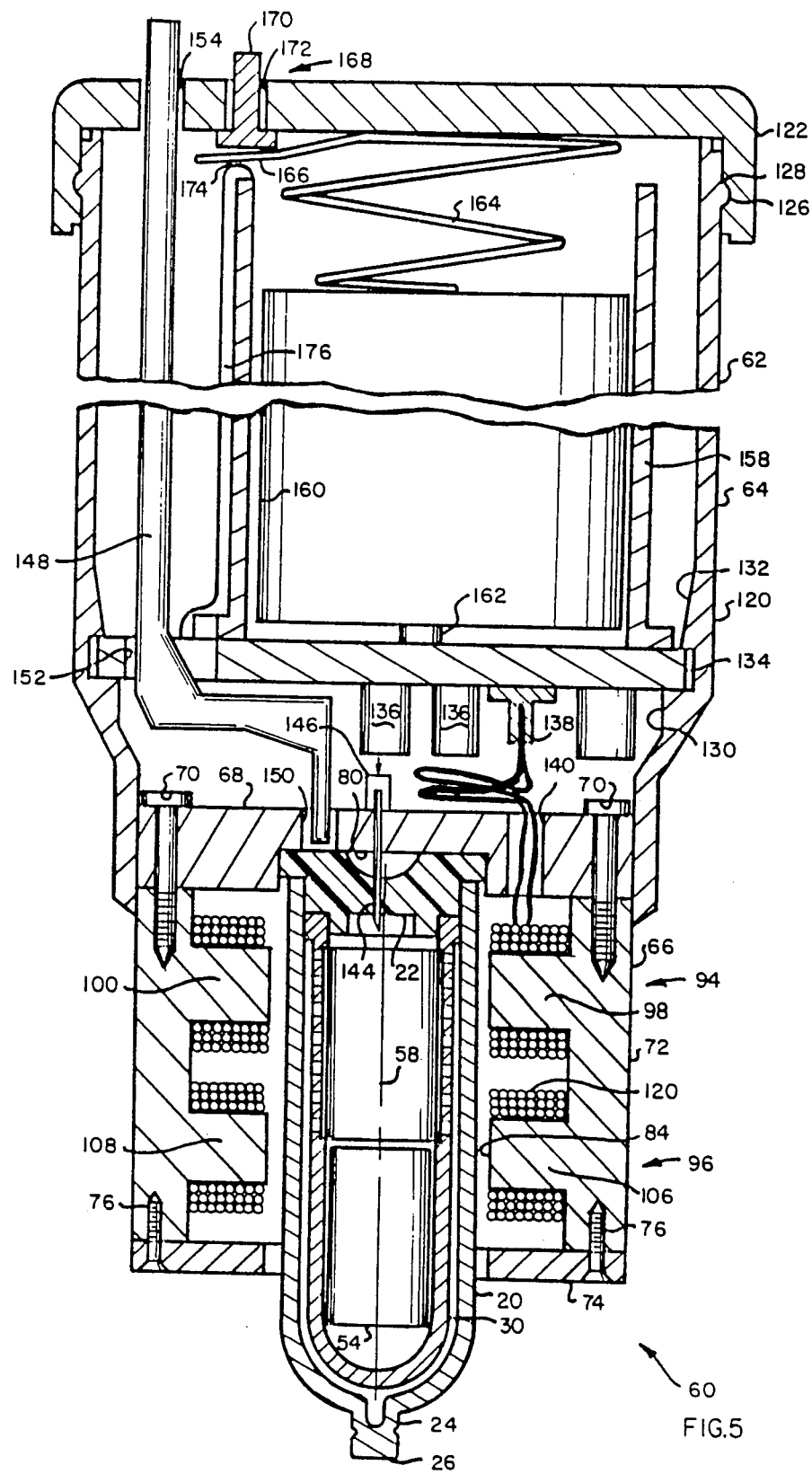
FIG. 5 is a sectional plan view of a rotor driver in accordance with the invention for rotationally driving a rotor within the container shown in FIGS. 2, 3 and 4.

A pair of lower and upper axially spaced flanges 130, 132 extend radially inward somewhat from the sidewall 124 to receive and support an electrical printed circuit board 134. Printed circuit board 134 supports an energization control circuit to provide the conventional timing and switching functions to energize the coils 120 to produce the rotating magnetic fields. The energization control circuit includes components 136 which are schematically represented as being affixed to the underside of printed circuit board 134, and a plug connector 138 which provides a plug connection to the four coil pairs 120. Since diametrically opposing pairs of coils may be wired in series, only eight connecting leads need be connected through plug connector 138. Somewhat fewer are shown in FIG. 5 to prevent obscuring the illustration with a multitude of wires. An axially extending aperture 140 is provided through the upper support plate 68 to facilitate the passage of the coil 120 energization leads through the support plate to the connector plug 138.

A vacuum release hollow needle 144 is secured to and extends through the support plate 68 to engage the rubber stopper 17 of a container 20 as it is inserted into the concavity 80. The needle 144 is optional and permits air to replace filtrate fluid as it passes through the membrane filter 32 to prevent creation of a partial vacuum within the interior of inner support tube 30. Such a partial vacuum would decrease the trans-membrane pressure and interfere with the filter process after enough filtrate fluid has passed from the interior to the exterior of inner support tube 30. The upper end of needle 144 is terminated by a one-way valve 146 which allows air to flow into the volume within inner support tube 30 while preventing internally generated pressure from forcing fluid upward and out through the needle 144. The design and construction of valve 146 is conventional and the details of valve 146 have therefore not been explicitly shown.

An ejection rod 148 passes through a hole 150 in upper support plate 68 to contact the top of rubber stopper 17. It also passes through a hole 152 in printed circuit board 134 and a hole 154 in upper cap 122 to provide access by an operator of the rotor driver 62. Upon pressing downward on the ejection rod 148, force is placed upon the top of rubber stopper 17 to dislodge the rubber stopper and hence the container from the rotor driver 62.

Mounted on the top side of printed circuit board 134 is a cylindrical battery housing 158 for receiving and supporting a plurality of standard D-cell batteries 160 storing the electrical energy required by an energization control circuit disposed on the bottom side of printed circuit board 134. Not shown is an electrical contact terminal on the top side of printed circuit board 134 for engaging a terminal 162 of a battery 160.

A conductive spring 164 extends between the batteries 160 and the cap 122 to urge the contact 160 into engagement with the terminal on printed circuit board 134. Spring 164 has a contact 166, which forms part of a push button switch 168 which further includes a push button 170 extending through an aperture 172 in upper cap 122 and a lower contact 174 mounted on a sidewall of battery housing 158 in the vicinity of the contact end 166. A conductive lead 176 provides an electrical connection from contact 174 down to the printed circuit board 134 where connection is provided to the energization control circuit on the underneath side of printed circuit board 134. Manual depression of switch 168 thus completes an energization circuit which enables the energization control circuit to begin generating the rotating magnetic fields required to rotationally drive the rotor 54.

It can thus be seen that, in operation, a container 20 is filled with a fluid sample such as blood in the usual manner with the container 20 being substituted for the traditional Vacutainer 11. Once filled with blood, the container 20 is suitably marked and sent to a laboratory for analysis. At the laboratory, the container 20 is inserted into the magnetic head 66 of the rotor driver 62 and the lower closure end 26 of fracture tip 24 is twisted and pulled to remove it and open the lower end of the container 20. The rotor driver is then held over a suitable container such as a dish for insertion into an automatic analysis system and the push button 170 is depressed to energize the energization control circuit and begin the filtration of plasma or serum from the fluid within the container 10. When a sufficient quantity of filtrate has been dispensed, the push button 170 is released to terminate the filtering process and the rotor driver is positioned over a suitable disposal container such as a trash can. The ejection rod 148 is then manually depressed to force the rubber stopper 17 out of engagement with the concavity 80 to permit the container 20 to drop into the disposal container for subsequent disposal.

It can thus be seen that the process of filtering and dispensing the filtrate fluid at the laboratory is greatly simplified. The laboratory technician is able to quickly and easily dispense the filtrate fluid and then dispose of the container 20 without ever being subjected to a danger of contamination. Instead of five to ten minutes of centrifugation followed by a delicate pipette transfer process, the filtrate fluid is automatically dispensed after a few seconds of filtering action and then the container 10 is dropped into an appropriate disposal container.

Figure 7:
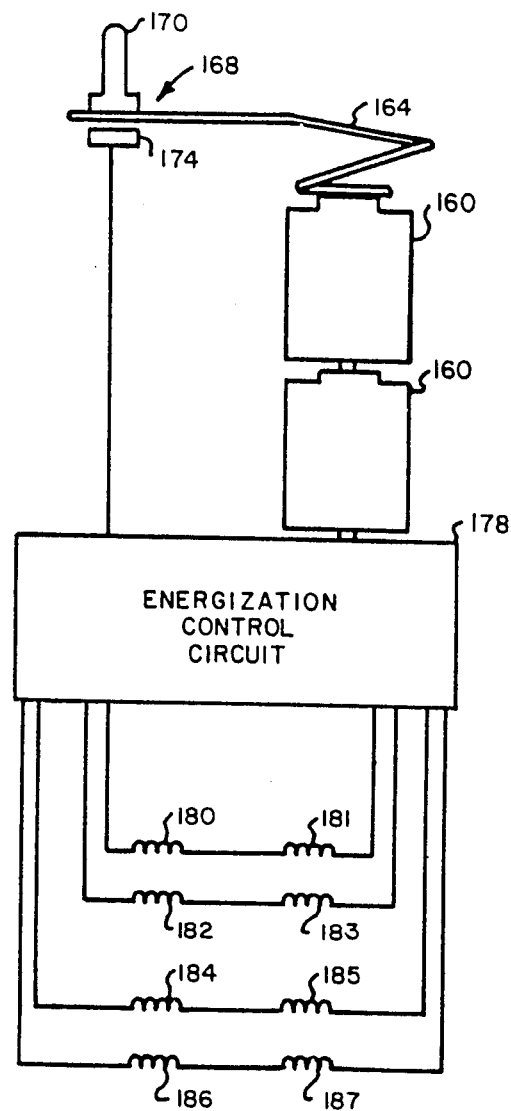
FIG. 7 is a schematic and block diagram representation of an electrical circuit used in the rotor driver shown in FIG. 5.

The circuitry for energizing the rotation coils 120 is illustrated in FIG. 7 in somewhat greater detail. It will be seen that an energization control circuit 178 is coupled to the batteries 160 through the manually operable switch 168. Energization control circuit 178 is also connected to series connected coil pair 180, 181 for coils 98, 100 respectively, and to coil pair 182, 184 for coils 102, 104, respectively. Similarly, at the lower position 96, coil pair 184, 185 for poles 106, 108 are connected to energization control circuit 178 along with coil pair 186, 187 for poles 110, 112, respectively.

Figure 8:
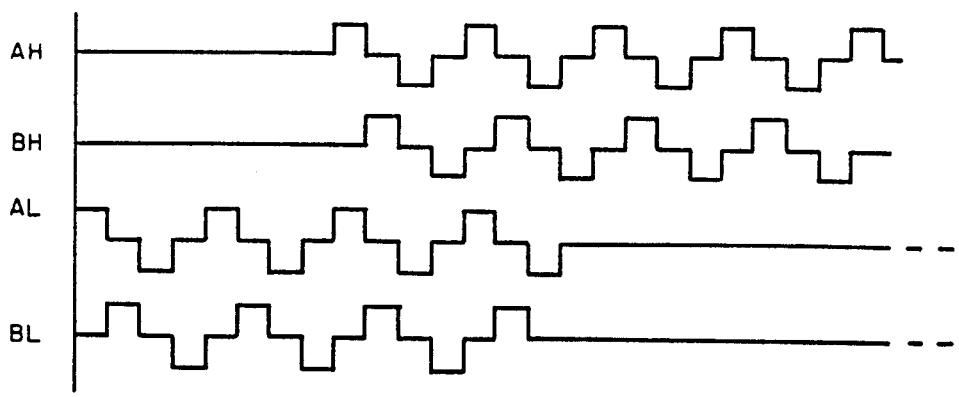
FIG. 8 is a graphical depiction of the energization of magnetic coils in the rotor driver shown in FIG. 5.
Figure 9:
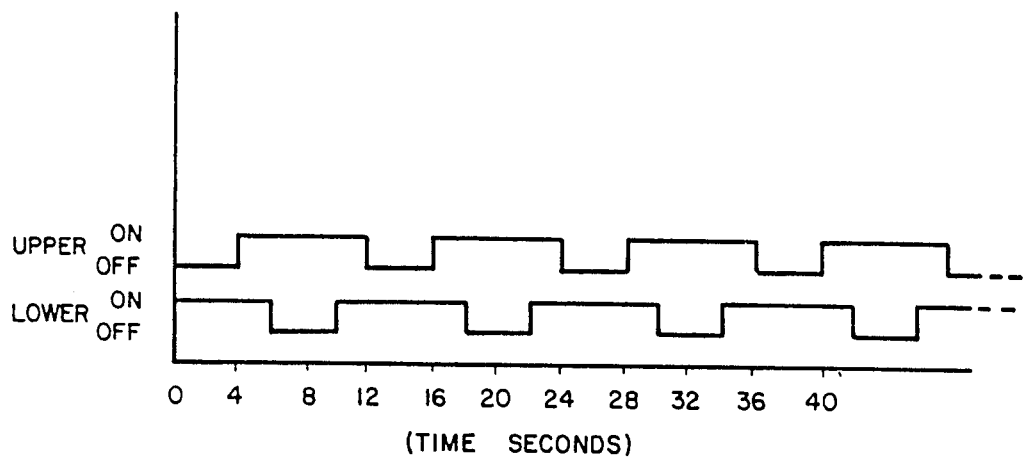
FIG. 9 is a further graphical depiction of the energization of magnetic coils in the rotor driver shown in FIG. 5.

While the specific circuits for implementing energization control circuit 178 have not been shown, it can be implemented with conventional switching and timing circuits using the timing relationships illustrated in FIGS. 8 and 9. The manner in which the coil pairs are energized to produce the rotating fields is illustrated in FIG. 8. In FIG. 8, the two upper pairs of coils are designated AH for coil pair 180, 181 and BH for coil pair 182, 184. Similarly, the two lower coil pairs are designated AL for coil pair 184, 185 and BL for coil pair 186, 187. Initially, the lower coil pairs are energized with pair AL initially being energized in a positive direction, which might, for example, create a magnetic field in a left to right (south to north) direction. Next, the AL pair is de-energized and the BL pair is energized to create a magnetic field in a top to bottom direction. Next, pair BL is de-energized and pair AL is energized with a negative polarity to generate a magnetic field in a right to left direction. Next, pair AL is de-energized and pair BL is energized with a negative polarity to generate a field in a bottom to top direction. This completes one rotation cycle and is subsequently repeated. After a suitable time, the upper coil pairs AH and BH are similarly energized in a rotating pattern that is synchronized with the lower coil pairs AL and BL. Rotating fields are thus generated which engage the permanent magnet field of rotor 54 and cause rotor 54 to rotate with the driving fields provided by rotor driver 62.

Referring now to FIG. 9, the up and down axial shuttle motion is induced as explained previously by alternately energizing the lower and upper winding pairs in approximately twelve-second repetitive cycles. In each case, a two-second overlap is provided after one upper or lower set of coils is energized before the other is de-energized. This helps provide a controlled oscillation of the rotor 54 as it moves up and down within the inner support tube 30 to create a transmembrane pressure to induce filtration of the fractionation fluid.

Various alternative arrangements of the rotor 54 which permit elimination of the third and fourth pole pairs at the lower axial position 96 of the magnetic drivehead 66 are illustrated in FIGS. 10-14. The arrangements shown in FIGS. 10-14 each provide for the recirculation or actual pumping of fractionation fluid so that the up and down oscillations of the rotor can be eliminated. While some of the arrangements shown in FIGS. 10-14 are less effective than the oscillatory pumping action, they are deemed adequate for only a few drops of filtrate fluid which are required for clinical analysis.

Figure 10:
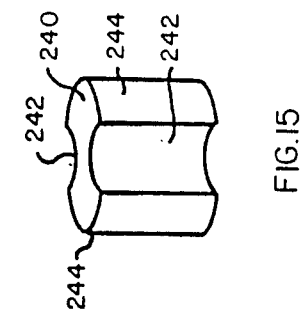
FIG. 10 is a perspective view of an alternative embodiment of a rotor used in the invention.
Figure 13:
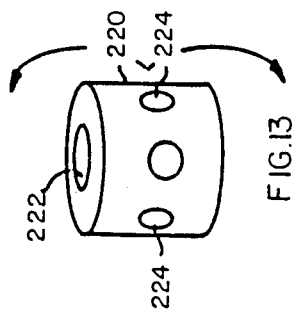
FIG. 13 is a perspective view of an alternative embodiment of a rotor used in the invention.

FIG. 10 illustrates a cylindrical rotor 200 which is substantially the same as rotor 54 except that it has an axially extending central bore 202. The rotor 200 can be utilized either in conjunction with an axially spaced two-level rotor driver as shown in FIG. 5 to provide increased circulation of fractionation fluid through the bore 200, or in conjunction with a single-level rotor driver with the bore 200 providing a small amount of recirculation to facilitate filtering action.

A rotor 206 shown in FIG. 10 has a plurality of axially extending channels or concavities formed in the outer circumference of the rotor and extending the full length of the rotor. The channels are substantially equally spaced about the circumference of the rotor 206. The channels 208 carry additional fractionation fluid to the vicinity of the filtration gap between the outer circumference of the rotor 206 and the filter membrane 32. The channels 208 in combination with a central bore 210 provide adequate circulation of fractionation fluid to obtain a small sample.

Figure 12:
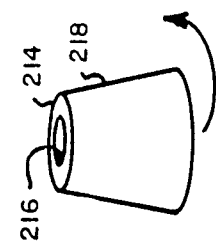
FIG. 12 is a perspective view of an alternative embodiment of a rotor used in the invention.

A rotor 214 shown in FIG. 12 has an axially extending central bore 216 and a tapered outer circumference 218. The tapered outer circumference produces a centrifugal pumping action which tends to cause the fractionation fluid to flow upward through the filtration gap and then downward through the central bore 216 to provide a recirculation of fractionation fluid through the filtration gap.

A rotor 220 is generally cylindrical in configuration with an axially extending central bore 22 and a plurality of radially extending bores 224 which are uniformly spaced about the circumference of the rotor 220 and axially positioned midway between the top and bottom thereof. The radially extending bores 224 produce a centrifugal pumping action which causes a continuous recirculation of fractionation fluid through the radially outward bores 224, and to the filtration gap and then axially upward and downward to flow back into the bores 222 which provides communication with the radially inward ends of the radially extending bores 224.

Figure 14:
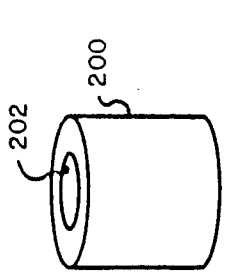
FIG. 14 is a perspective view of an alternative embodiment of a rotor used in the invention.

A rotor 230 shown in FIG. 14 has a plurality of axially extending channels formed in the periphery thereof, which are shaped to provide cup shaped concavities at the leading edges of extremities 234 which define the cylindrical outer shape of rotor 230. The channels 232 make additional fractionation fluid available to the filtration gap and assure sufficient mixing to produce a small quantity of filtrate fluid. The channels 232 also serve to produce a centrifugal pumping action which increases the fractionation fluid pressure within the filtration gap to produce a trans-membrane pressure differential sufficient to assure proper filter action.

Figure 15:
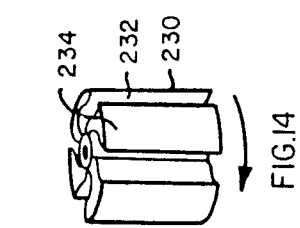
FIG. 15 is a perspective view of an alternative embodiment of a non-magnetized high permeability rotor as used in the invention.
Figure 11:
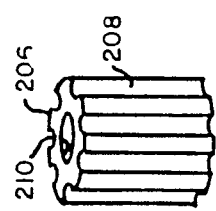
FIG. 11 is a perspective view of an alternative embodiment of a rotor used in the invention.

As an alternative to the above-described permanent magnetic rotors, FIG. 15 illustrates a rotor that does not contain a permanent magnetic field at all, but is composed at least in part by a ferromagnetic material which will respond to an external magnetic field—such as described in Patent Application Ser. No. 727,585 filed Apr. 26, 1985, by Donald W. Schoendorfer. The generally cylindrical rotor 240 has two axially extending, diametrically opposed concavities 242 which define two diametrically opposed axially extending salient poles 244. The rotor 240 provides a cost advantage over the magnetized rotors. Since the rotor is part of the disposable container it is important to keep the cost as low as possible. Likewise, the driving force to generate rotation may not be solely based on magnetic energy, but may alternatively be provided by some other form of energy coupling from an external source. For example, repulsive electrical fields or some combination of electrical and magnetic fields may provide the required rotational energization of the rotor end.

While there have been described and shown above particular embodiments of a fluid separation system including a disposable fluid filtration container and a rotor driver for the purpose of enabling a person skilled in the art to make and use the invention, it will be appreciated that the invention is not limited thereto. Accordingly, any modifications, variations or equivalent arrangements within the scope of the attached claims should be considered to be within the scope of the invention.

What is claimed is:

1. The method comprising filtering liquid from a suspension using a spinner having a generally cylindrical outer surface and a concentric filter membrane separated from the outer surface by a gap by, rotating the spinner about a central axis, with the surface of the spinner being adjacent the concentric membrane, the relative surface velocity of the spinner and the gap being selected to establish dynamic motion in the suspension, and oscillating the spinner along the central axis to develop internal pressure in the suspension for urging filtrate through the membrane.

2. The method as set forth in claim 1 wherein the suspension is whole blood and the filtrate is plasma.

3. The method as set forth in claim 1 wherein the relative surface velocity of the spinner and the magnitude of the gap between the spinner and membrane establish a shear in excess of 2000 $sec^{-1}$ and vortices in the suspension.

4. The method of filtration according to claim 1 wherein the size of the gap and the rotational velocity of the spinner are selected in conjunction with the characteristics of the liquid to produce a Taylor number of approximately 156.

5. The method of filtering according to claim 1 wherein the size of the gap and the rotational velocity of the spinner are selected in conjunction with the characteristics of the liquid to produce a Taylor number of approximately 156 and a Reynolds number of approximately 550.

6. The method of filtering according to claim 1 wherein the size of the gap and the rotational velocity of the spinner are selected in conjunction with the characteristics of the liquid to produce a Taylor number of approximately 156, a Reynolds number of approximately 550 and a shear rate of approximately 8860 per second.

7. The method of filtration according to claim 1 further comprising the steps of disposing the spinner and liquid within a closed volume that is at least partly defined by the filter membrane before rotating and oscillating the spinner.

8. The method of filtration according to claim 7 wherein the spinner is disposed axle free within the closed volume and further comprising the step of generating externally of the closed volume a rotating energy field which interacts with and rotationally drives the spinner.

* * * * *